United States Patent [19]

Vanlerberghe et al.

[11] Patent Number: 4,465,860

[45] Date of Patent: Aug. 14, 1984

[54] POLYOXYETHYLENEATED NON-IONIC SURFACE-ACTIVE AGENTS WITH TWO LIPOPHILIC CHAINS

[75] Inventors: Guy Vanlerberghe, Claye-Souilly; Henri Sebag, Paris, both of France

[73] Assignee: Societe Anonyme dite: L'Oreal, Paris, France

[21] Appl. No.: 451,734

[22] Filed: Dec. 21, 1982

Related U.S. Application Data

[62] Division of Ser. No. 196,276, Oct. 14, 1980, Pat. No. 4,399,313.

[30] Foreign Application Priority Data

Oct. 16, 1979 [FR] France .............................. 79 25641

[51] Int. Cl.³ ............................................ C07C 147/14
[52] U.S. Cl. ........................................ 568/37; 568/36; 568/45; 568/50
[58] Field of Search ....................... 568/36, 37, 45, 50

[56] References Cited

U.S. PATENT DOCUMENTS 3,988,377 10/1976 Lamberti et al. ..................... 568/36
4,266,080 5/1981 Falk et al. ............................ 568/50
4,330,677 5/1982 Linke et al. .......................... 568/45

Primary Examiner—Donald G. Daus
Assistant Examiner—M. C. Eakin
Attorney, Agent, or Firm—Cushman, Darby & Cushman

[57] ABSTRACT

Non-ionic products of the formula:

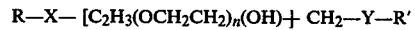

in which R and R' denote alkyl or alkenyl radicals having from 6 to 20 carbon atoms, the sum of the numbers of carbon atoms in R and R' being 24 to 32; X denotes an oxygen atom, a sulphur atom or a sulphoxide group; Y denotes a sulphur atom, a sulphoxide group or a methylene group (if Y denotes methylene, the sum of the numbers of carbon atoms in R and R' is 22 to 30); and n denotes an integer or decimal number from 1 to 40 are disclosed. These non-ionic compounds are suitable for use in pharmaceutical or cosmetic applications, in particular for the care of the skin or hair.

6 Claims, No Drawings

POLYOXYETHYLENEATED NON-IONIC SURFACE-ACTIVE AGENTS WITH TWO LIPOPHILIC CHAINS

This is a division of application Ser. No. 196,276, filed Oct. 14, 1980, now U.S. Pat. No. 4,399,313.

DESCRIPTION

This invention relates to polyoxyethyleneated non-ionic surface-active agents, compositions in which they are present and, in particular, the use of these compositions in the cosmetic or pharmaceutical industry for the care and treatment of the face, body or head of hair.

U.S. Pat. No. 3,943,178 describes a family of polyethoxylated secondary alcohols. These compounds, which are recommended for use in the bleaching of textiles, have relatively short alkyl groups and have proved to be rather unsuitable for pharmaceutical or cosmetic compositions.

We have found, in particular, that these compounds are rather ineffective as emulsifiers and are not well tolerated from the physiological point of view, as a result of tests involving instillation into rabbits' eyes and on lytic activity towards membranes of certain cells, such as red blood corpuscles.

We have discovered compounds or products, some of which have a structure similar to that of the compounds described in the abovementioned patent, but which contain substantially longer hydrocarbon chains than the hydrocarbon chains of these compounds.

We have found that, surprisingly, these compounds have a surface activity, as emulsifiers, which is superior to that of the compounds described in this U.S. patent. Moreover, in contrast to the compounds of U.S. Pat. No. 3,943,178, the compounds according to the invention are well tolerated physiologically.

The products according to the present invention are essentially characterised in that they correspond to the formula (I):

$$R-X-[C_2H_3(OCH_2CH_2)_n(OH)]-CH_2-Y-R' \quad (I)$$

in which R and R' denote alkyl or alkenyl radicals having from 6 to 20 carbon atoms, the sum of the numbers of carbon atoms in R and R' being 24 to 32; X denotes an oxygen atom, a sulphur atom or a sulphoxide group; Y denotes a sulphur atom, a sulphoxide group or a methylene group (if Y denotes a methylene group, the sum of the carbon atoms in R and R' is 22 to 30); and n denotes an integer or decimal number from 1 to 40 and preferably 5 to 30.

R' preferably denotes a linear alkyl radical. Y preferably denotes —$CH_2$—.

The products which are more particularly preferred are those in which R and R' are chosen from hexyl, octyl, decyl, dodecyl, tetradecyl, hexadecyl, octadecyl and eicosyl radicals; in these preferred products, R can also denote: 2-ethylhexyl, 2-hexyldecyl, 2-octyldodecyl, 1-methylundecyl, 1-methyldodecyl, 1-methyltridecyl, 1-methyltetradecyl, 1-methylpentadecyl, undecenyl and oleyl.

These products can be prepared in accordance with a process comprising two steps.

The first step consists in preparing intermediates with an alcohol group, corresponding to the formula:

$$R-X_1-[C_2H_3(OH)]-CH_2-Y_1R' \quad (II)$$

in which R and R' have the meanings indicated above, $X_1$ denotes an oxygen or sulphur atom and $Y_1$ denotes —$CH_2$— or a sulphur atom.

These products of the formula (II) can be obtained by reacting a compound containing active hydrogen:

$$RX_1H \quad (III)$$

with a compound containing a terminal oxirane group corresponding to the formula:

$$R'-Y_1-CH_2-CH\underset{O}{\overset{}{\diagdown\diagup}}CH_2 \quad (IV)$$

This reaction is preferably carried out in the presence of a molar excess of product (III), relative to the compound (IV), it being possible for this excess to be as much as, say, 10 times the stoichiometric amount, either in the presence of an acid catalyst, such as $BF_3$, $SnCl_4$ or $ZnCl_2$, or in the presence of an alkaline catalyst, such as sodium, potassium or the methylate, ethylate or tert.-butylate of sodium or potassium. With acid catalysis, the reaction temperature is conveniently 40° to 100° C.; with alkaline catalysis, it is suitably 80° to 180° C.

When one of the groups $X_1$ or $Y_1$ or both denote a sulphur atom, the reaction is preferably carried out with alkaline catalysis.

The proportion of catalyst used is generally from 0.1 to 10%, preferably 0.2 to 3%, by weight in the case of acid catalysts and from 1 to 8% by weight in the case of alkaline catalysts.

If desired, the excess of the compound containing active hydrogen, of formula (III), can be removed under reduced pressure after the reaction. Depending on the direction of opening of the epoxide IV, the two possible isomers II(a) and II(b) can be obtained:

$$R-X_1-CH_2-\underset{OH}{\overset{}{C}H}-CH_2-Y_1-R' \quad II(a)$$

$$R-X_1-\underset{CH_2OH}{\overset{}{C}H}-CH_2-Y_1-R' \quad II(b)$$

For the products of this invention, this results in the two families I(a) and I(b), which can be present simultaneously:

$$R-X-CH_2-\underset{(OCH_2CH_2)_nOH}{\overset{}{C}H}-CH_2-Y-R' \quad I(a)$$

and $$R-X-\underset{CH_2-(OCH_2CH_2)_nOH}{\overset{}{C}H}-CH_2-Y-R' \quad I(b)$$

The intermediates of formula (II) are generally purified by distillation under reduced pressure, but, if desired, the crude reaction products can be used for the second step provided that the products with more than two fatty chains do not represent more than, say, 50% by weight.

These higher molecular weight products, the constitution of which can be represented by the formula:

$$R-X_1[C_2H_3(CH_2Y_1R')O]_{\overline{x}}H \qquad (V)$$

in which x most frequently denotes 2 and, sometimes, 3, apparently do not detract from the properties of the products of this invention, provided that the amount remains limited.

The proportions of the products of formula (V) are generally the lower, the greater is the excess of the compound containing active hydrogen of formula (III).

During the second step, the intermediates (II) are oxyethyleneated. The polyaddition reaction with ethylene oxide can be carried out initially in the presence of an acid catalyst, such as $BF_3$, and then in the presence of an alkaline catalyst, for example one of those mentioned above.

The oxyethyleneation reaction can also be carried out completely with alkaline catalysis; this is preferred when the compounds of formula (II) contain a thioether group.

The oxyethyleneation reaction is generally carried out at a temperature of 40° to 110° C. with acid catalysis or at 120° to 180° C. with alkaline catalysis.

When this reaction is carried out in two stages, the acid catalyst can immediately be neutralised and removed by washing with water. This washing also serves to remove the polyethylene glycols which may have been formed.

The purpose of using an acid catalyst for the first part of the oxyethyleneation reaction is to convert a greater proportion of products (II) whilst at the same time forming products with a primary alcohol group which are more reactive than the products (II) with a secondary alcohol group.

It will be appreciated that the products will normally be in the form of mixtures of compounds with different numbers of oxyethylene units.

The unreacted intermediates and the compounds of formula (II) in which n is small can be removed by molecular distillation, if desired, preferably after the acid-catalysed reaction or also at the end of the oxyethyleneation reaction.

The final products are preferably washed with hot water, even if they are water-soluble. In the latter case, butan-1-ol, butoxyethanol or butoxyethoxyethanol can be used as a co-solvent in order to facilitate the salting-out of the products according to the invention.

The oxyethyleneated compounds derived from the products of formula (II), containing at least one thioether group, can be oxidised with hydrogen peroxide at, say, 30°–50° C., the thioether groups thus being converted to sulphoxide groups.

The products, according to the invention, corresponding to formula (I) are in the form of oils, semi-liquid products or yellow-coloured or brown-coloured waxes.

Depending on the length of the hydrocarbon chains and on the average number n of ethoxy units, the products will either be principally lipophilic or hydrophilic. The shorter the hydrocarbon chains and the greater the degree of oxyethyleneation n, the more pronounced will be the hydrophilic character.

The products according to the invention can advantageously be used in cosmetic or pharmaceutical compositions as emulsifiers for water-in-oil or oil-in-water emulsions, as self-dispersing or self-emulsifying products, as solubilising agents, as vehicles for active products, such as products for the treatment of the skin or head of hair, as make-up removal products or as low-foaming cleansing products.

Examples of cosmetic compositions which may be mentioned in particular are shampoos, rinses, wavesetting lotions, brushing lotions, perming or colouring compositions, make-up foundations, eye make-up removal lotions, make-up removal milks, face milks, body milks, body emulsions, toning emulsions, neutral make-up bases, anti-sunburn compositions, antiperspirant creams, deodorant creams, and moisturising compositions.

The products of formula (I) can thus be used in compositions in the form of, for example, aqueous or aqueous-alcoholic solutions or dispersions, creams, milks, compacts or sticks, or packaged in the form of aerosols.

In addition to the vehicle and products of formula (I), the cosmetic compositions according to the invention can contain other constituents, such as non-ionic, anionic, cationic, amphoteric, and zwitterionic surface-active agents, non-ionic, anionic, cationic and amphoteric resins, preservatives, sequestering agents, perfumes, agents for providing protection against ultra-violet radiation, animal, vegetable, mineral and synthetic oils, fatty acids, fatty acid esters, solvents, such as alcohols having from 1 to 6 carbon atoms, glycols and glycol ethers, opacifiers, thickeners, dyestuffs, pigments, pH modifiers, natural products, plant extracts, mineral salts, and active substances which can have an effect on the treatment, care or protection of the skin or hair.

In an aqueous medium, the products according to the invention can form the walls of small lipid spheres which can be used for carrying the active products, notably cosmetic or pharmaceutical active products. Apart from the substance to be carried, the products can be associated, in this case, with compounds which can modify the permeability of the lipid capsule which they form around the active substance. Amongst these compounds which modify the permeability of the lipid capsule, sterols, such as cholesterol or sitosterol, and ionic lipid compounds, such as sodium dicetyl-phosphate or dimethyldistearylammonium chloride or bromide, may be mentioned.

Amongst the active products which can be carried in the lipid membranes, there may be mentioned moisturisers, artificial bronzing agents for the skin, sun filters, antiperspirants, deodorants, astringents, scented water, freshening products, toners, cicatrising agents, keratolytics, depilatories, animal or plant tissue extracts, water-soluble dyestuffs, anti-dandruff agents, anti-seborrhoea agents and reducing agents.

Amongst pharmaceutical active products, there may be mentioned: vitamins, hormones, enzymes, vaccines, anti-inflammatory products, antibiotics and bactericides.

The process for the preparation of small lipid spheres is described in French Specification No. 2,315,991, British Specification No. 1,539,625, Canadian Pat. No. 1,063,908, Belgian Patent No. 843,300 and U.S. Pat. No. 4,217,344, the disclosure of which is hereby incorporated by reference.

If they are used for the treatment of the skin or hair, the products according to the invention are essentially used for their dispersing, emulsifying, emollient, or cleansing action, in particular for the eyes and face.

They can also be used, by virtue of their neutral behaviour, as a pharmaceutical excipient.

The products according to the invention are generally present in an amount from 0.2% to 50%, and preferably 0.5% to 25%, of the total weight of the cosmetic or pharmaceutical composition.

The invention also provides a process for the treatment of the hair or skin, which consists in applying, to the hair or to the skin, an appropriate amount of a composition of the present invention.

The following Examples further illustrate the present invention.

EXAMPLE 1

Preparation of a mixture of compounds, of the formula:

$$C_{10}H_{21}-O-[C_2H_3(OCH_2CH_2)_n(OH)]-CH_2-CH_2-C_{12}H_{25} \quad (1)$$

in which n denotes an average statistical value of 4.6.

(a) Preparation of the intermediate of the formula:

$$C_{10}H_{21}-O-[C_2H_3(OH)]-CH_2-CH_2-C_{12}H_{25} \quad (2)$$

12.8 g (75 meq (milliequivalents)) of sodium methylate, dissolved in methanol, are added to 711 g (4.5 mols) of decan-1-ol marketed under the name "Alfol 10" by CONDEA.

The methanol is removed by heating under reduced pressure.

The residue is heated to a temperature of 150° C. and 360 g, i.e. 1.5 mols, of 1,2-epoxyhexadecane, sold under the trademark "Epoxide 16" by UNION CARBIDE, are added in the course of about 2 hours.

The temperature of 150° C. is maintained for 3 hours 30 minutes after the addition.

The product thus obtained is washed twice with its own weight of boiling water, and the excess water and alcohol are then evaporated off under reduced pressure.

The product thus obtained is distilled at a temperature of 187°–195° C. under a pressure of 0.07 mm Hg.

The intermediate is in the form of a white wax having a melting point of 50° C.

Hydroxyl number: 2.40–2.32 meq/g.

(b) Preparation of a mixture of compounds of the formula (1).

0.1 ml of BF$_3$ etherate is added to 40 g (0.1 mol) of the compound of the formula (2), prepared in stage (a), in the molten state.

The reaction mixture is heated to 75° C. under a nitrogen atmosphere, and a stream of gaseous ethylene oxide is then passed in until the increase in weight of the reaction mixture is 28 g (0.63 mol of ethylene oxide).

The product is subsequently washed twice with its own weight of hot water and then dried by heating under reduced pressure.

The value of n, which is the average number of ethoxy units per mol of compound, is 4.6. This value is determined by nuclear magnetic resonance (NMR).

Hydroxyl number: 1.43–1.31 meq/g.

EXAMPLE 2

Preparation of a mixture of compounds, of the formula:

$$C_{10}H_{21}-O-[C_2H_3(OCH_2CH_2)_n(OH)]-CH_2-CH_2-C_{12}H_{25} \quad (3)$$

in which n denotes an average statistical value of 10.

1.2 g of sodium methylate, dissolved in methanol (5.85 meq/g), are added to 50 g (0.083 mol) of the product prepared in accordance with Example 1(b), in the molten state. The mixture is heated to 150° C. and gaseous ethylene oxide is passed in until the increase in weight of the reaction mixture is 20 g (that is to say 0.45 mol of ethylene oxide).

The product is solubilised in its own weight of n-butan-1-ol and the mixture is washed twice with an equivalent weight of boiling water. The butanol is evaporated off under reduced pressure. The product thus obtained is semi-liquid at ambient temperature.

The cloud point of a solution of 5% strength by weight, in a butyldiglycol/water mixture containing 25% by weight of butyldiglycol, is 75° C.

The value of n, determined by NMR, is 10.

EXAMPLE 3

Preparation of a mixture of compounds, of the formula:

$$C_{10}H_{21}-O-[C_2H_3(OCH_2CH_2)_n(OH)]-CH_2-CH_2-C_{12}H_{25} \quad (4)$$

in which n denotes an average statistical value of 15.

0.4 ml of BF$_3$ etherate is added to 100 g (0.25 mol) of the compound prepared in accordance with Example 1(a) and in the molten state, and the mixture is then heated to 75° C. under a nitrogen atmosphere. 72 g of gaseous ethylene oxide are then condensed into the mixture. The resulting product is washed twice with 180 to 200 ml of boiling water. (45 ml of isopropanol are added during the first washing in order to facilitate the separation of the organic phase.)

The material is then dried under reduced pressure. The resulting product is liquid at ambient temperature.

3.4 g (20 meq) of a solution of sodium methylate in methanol are added to 140 g of this product. The methanol is removed by heating under reduced pressure. The reaction mixture is heated to a temperature of 160° C. and ethylene oxide is introduced, the temperature being kept between 160° and 190° C.

After the condensation of 96 g (2.18 mols) of ethylene oxide, the product is solubilised in 230 g of n-butan-1-ol and the mixture is washed twice with 500 ml of boiling water.

The organic phase separated off is dried under reduced pressure and the traces of n-butanol are removed by azeotropic distillation. The most volatile fractions (about 15% by weight) are separated off by molecular distillation at 250° C. under a pressure of 10$^{-3}$ mm Hg.

The residue thus obtained is in the form of a pale yellow oil which is semi-pasty at ordinary temperature and dissolves in water to give a very slight opalescence.

The value of n, determined by NMR, is 15.

The cloud point of a solution of 0.5% strength by weight, in water, is 60° C.

EXAMPLE 4

Preparation of a mixture of compounds, of the formula:

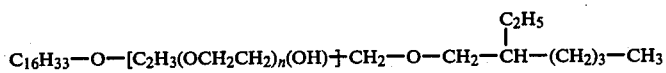

$$C_{16}H_{33}-O-[C_2H_3(OCH_2CH_2)_n(OH)]-CH_2-O-CH_2-\overset{C_2H_5}{\underset{|}{CH}}-(CH_2)_3-CH_3 \quad (5)$$

in which n denotes an average statistical value of 10.

(a) Preparation of the intermediate of the formula:

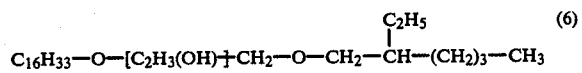

$$C_{16}H_{33}-O-[C_2H_3(OH)]-CH_2-O-CH_2-\overset{C_2H_5}{\underset{|}{CH}}-(CH_2)_3-CH_3 \quad (6)$$

4.8 g of a solution of sodium methylate in methanol (30 meq) are added to 500 g (2 mols) of molten hexadecan-1-ol. The temperature is raised to 150° C. under a nitrogen atmosphere and 186 g (1 mol) of 2-ethylhexyl glycidyl ether are added. The reaction mixture is kept at 150° C. for a further 4 hours after the end of the addition and the excess alcohol is then distilled under reduced pressure.

The remaining product is neutralised with hydrochloric acid and then washed with twice its own weight of boiling water.

After drying by heating under reduced pressure, the most volatile fractions are separated off by molecular distillation at 130° C. under a pressure of $10^{-3}$ mm Hg.

The residue is subsequently distilled at 220° C./$10^{-3}$ mm Hg and then rectified at 175° C./$10^{-2}$ mm Hg.

This yields a colourless oil having a melting point of 9°–10° C. and a hydroxyl number of 2.27 meq/g.

(b) 0.08 ml of BF$_3$ etherate is added to 34.2 g (0.08 mol) of the intermediate prepared in step (a) and the mixture is heated to a temperature of 75° C. under a stream of nitrogen.

Ethylene oxide is then added until the increase in weight of the reaction mixture is 12 g (0.27 mol). 1.4 g of sodium methylate, dissolved in methanol (5.85 meq/g), are then introduced, and, after the methanol has been removed by heating under reduced pressure, the mixture is heated to 160° C. and a further 28 g (0.63 mol) of ethylene oxide are added.

This yields a light yellow water-dispersible paste which is washed three times with 100 ml of boiling water.

After drying under reduced pressure, a yellow oil is obtained.

The cloud point of a solution of 5% strength by weight, in a butyldiglycol/water mixture containing 25% by weight of butyldiglycol, is 74° C.

The value of n, determined by NMR, is 10.

EXAMPLE 5

Preparation of a mixture of compounds, of the formula:

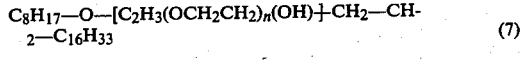

$$C_8H_{17}-O-[C_2H_3(OCH_2CH_2)_n(OH)]-CH_2-CH_2-C_{16}H_{33} \quad (7)$$

in which n denotes an average statistical value of 5.6.

(a) Preparation of the intermediate of the formula:

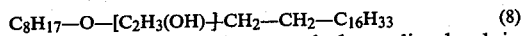

$$C_8H_{17}-O-[C_2H_3(OH)]-CH_2-CH_2-C_{16}H_{33} \quad (8)$$

8.5 g (50 meq) of sodium methylate, dissolved in methanol, are added to 390 g (3 mols) of n-octanol. The methanol is removed by heating under reduced pressure, the temperature is then raised to 150° C. under a nitrogen atmosphere and 268 g (1 mol) of 1,2-epoxyoctadecane are added dropwise. After the addition, the temperature is kept at 150° C. for 3 hours 30 minutes and the product is then washed three times with 800 ml of boiling water.

The organic phase is heated under reduced pressure in order to remove the excess water and octanol.

The residue is distilled under a pressure of 0.1 mm Hg at a temperature of 193° C.–205° C.

The resulting product is a white solid having a melting point of 49° C.

(b) 0.4 ml of BF$_3$ ethereate is added to 95 g of the intermediate prepared in step (a) and in the molten state, and the mixture is then heated to 80° C. under a nitrogen atmosphere. Ethylene oxide is then added until the increase in weight of the reaction mixture is 47 g (1.06 mols).

The product thus obtained is washed twice with 200 ml of boiling water. The organic phase is dried by heating under reduced pressure.

The most volatile compounds (45% of the reaction mixture) are separated off by molecular distillation at 175° C. The residue is in the form of a colourless waterdispersible liquid. The value of n, determined by NMR, is 5.6.

The hydroxyl number is 1.30–1.35 meq/g.

The cloud point of a solution of 5% strength by weight, in a butyldiglycol/water mixture containing 25% by weight of butyldiglycol, is 58° C.

EXAMPLE 6

Preparation of a mixture of compounds, of the formula:

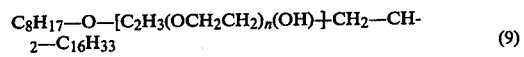

$$C_8H_{17}-O-[C_2H_3(OCH_2CH_2)_n(OH)]-CH_2-CH_2-C_{16}H_{33} \quad (9)$$

in which n represents an average statistical value of 18.

0.5 ml (2.5 meq) of sodium methylate, dissolved in methanol, is added to 22.5 g (0.034 mol) of the mixture of compounds prepared in accordance with Example 5(b). The methanol is removed by heating under reduced pressure and the reaction mixture is then heated to 160° C. Gaseous ethylene oxide is introduced into this medium until the increase in weight of the reaction mixture is 19 g, which corresponds to 0.43 mol of ethylene oxide.

The resulting product is dissolved in 30 ml of n-butan-1-ol and the solution is washed twice with 70 ml of boiling water. The organic phase is dried by heating under reduced pressure. This yields a paste of low consistency, which is pale yellow in colour and watersoluble.

The cloud point of a solution of 0.5% strength by weight, in demineralised water, is 80° C. The cloud point of a solution of 0.5% strength by weight, in salt water containing 10% of NaCl, is 52° C.

The value of n, determined by NMR, is 18.

EXAMPLE 7

Preparation of a mixture of compounds, of the formula:

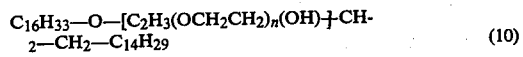

$$C_{16}H_{33}-O-[C_2H_3(OCH_2CH_2)_n(OH)]-CH_2-CH_2-C_{14}H_{29} \quad (10)$$

in which n denotes an average statistical value of 3.

(a) Preparation of the intermediate of the formula:

$$C_{16}H_{33}—O—[C_2H_3(OH)]—CH_2—CH_2—C_{14}H_{29} \quad (11)$$

5.1 g (30 meq) of a solution of sodium methylate in methanol are added to 435.6 (1.8 mols) of hexadecanol (marketed under the name "Alfol 16" by CONDEA) in the molten state.

The methanol is distilled under reduced pressure, the mixture is heated to 145° C. under a nitrogen atmosphere and 162 g (0.6 mol) of 1,2-epoxyoctadecane are then added dropwise.

The reaction mixture is kept at 145° C. for 3 hours and is then washed three times with 500 ml of boiling water.

The organic phase is dried by heating under reduced pressure. The excess alcohol is distilled under reduced pressure and the volatile products are then removed by molecular distillation at 150° C./10$^{-3}$ mm Hg. The product is then distilled at 210° C./10$^{-3}$ mm Hg. This yields a white wax having a melting point of 70° C. (b) 1.5 ml (7.5 meq) of a solution of sodium methylate in methanol are added to 76.5 g (1.15 mols) of the compound prepared above and in the molten state. The methanol is distilled by heating under reduced pressure, the mixture is then heated to a temperature of 170° C. and 30 g of ethylene oxide are added.

The resulting crude product is then washed twice with 100 ml of boiling water, 20 ml of n-butan-1-ol being added during each washing in order to assist decantation. After distillation of the solvents under reduced pressure, a wax which is pale yellow in colour is obtained.

The value of n, determined by NMR, is 3.

EXAMPLE 8

Preparation of a mixture of compounds, of the formula:

$$C_{16}H_{33}—O—[C_2H_3(OCH_2CH_2)_n(OH)]—CH_2—CH_2—C_{14}H_{29} \quad (12)$$

in which n denotes an average statistical value of 9.

0.7 ml (3.75 meq) of a solution of sodium methylate in methanol is added to 53 g (0.082 mol) of the crude mixture of compounds prepared in Example 7(b) and in the molten state.

The methanol is distilled under reduced pressure, the mixture is then heated to 170° C. under a nitrogen atmosphere and gaseous ethylene oxide is introduced until the increase in weight of the reaction mixture is 30 g.

The product is washed twice with 100 ml of boiling water. 40 ml of n-butan-1-ol are added during the second washing in order to facilitate decantation. The resulting product is dried by heating under reduced pressure and the traces of n-butan-1-ol are then removed by azeotropic distillation.

This yields a yellow wax. The average number n, determined by NMR, is 9.

The cloud point of a solution of 5% strength by weight, in a butyldiglycol/water mixture containing 25% by weight of butyldiglycol, is 79° C.

EXAMPLE 9

Preparation of a mixture of compounds of the formula:

$$C_{16}H_{33}—O—[C_2H_3(OCH_2CH_2)_n(OH)]—CH_2—CH_2—C_{14}H_{29} \quad (13)$$

in which n denotes an average statistical value of 25.

44 g of the crude product (before washing) prepared in Example 8 are heated to 160° C. 36 g (0.82 mol) of ethylene oxide are then introduced therein under a nitrogen atmosphere. This yields a waxy product which is solubilised in 50 ml of n-butan-1-ol, and the solution is washed twice with 100 ml of boiling water. The organic solution is dried by heating under reduced pressure and this yields a yellow wax having a dropping point of 42° C.

The value of n, determined by NMR, is 25.

The cloud point of a solution of 5% strength by weight, in a butyldiglycol/water mixture containing 25% by weight of butyldiglycol, is 87° C.

EXAMPLE 10

Preparation of a mixture of compounds, of the formula:

$$C_{12}H_{25}—S—[C_2H_3(OCH_2CH_2)_n(OH)]—CH_2CH_2—C_{12}H_{25} \quad (14)$$

in which n denotes an average statistical value of 12.5.

(a) Preparation of the intermediate of the formula:

$$C_{12}H_{25}—S—[C_2H_3(OH)]—CH_2—CH_2—C_{12}H_{25} \quad (15)$$

5 ml of a solution of sodium methylate in methanol (25 meq) are added, at ordinary temperature, to 80 g (0.4 mol) of dodecanethiol. The methanol is distilled under reduced pressure, the reaction mixture is heated to 65° C. and 92 g (0.36 mol) of 1,2-epoxyhexadecane are added under a nitrogen atmosphere.

The reaction mixture is kept at 70° C. for 45 minutes and is then washed three times with 200 ml of boiling water, in the presence of 120 ml of isopropanol and dilute HCl in order to remove the catalyst. The resulting product is dried by heating under reduced pressure and then distilled at 226°–230° C./0.05 mm Hg. Recrystallisation is carried out from absolute ethanol.

This yields a white wax having a melting point of 50° C.

(b) 1.5 ml of a solution of sodium methylate in methanol are added to 29 g (0.065 mol) of the product obtained in step (a) and in the molten state. The methanol is distilled under reduced pressure and the mixture is then heated to 160° C. under a nitrogen atmosphere. 59 g of ethylene oxide, that is to say 1.34 mols, are added.

The crude product thus obtained is dissolved in an equal weight of n-butan-1-ol and the solution is washed twice with 100 ml of boiling water. The organic solution is then dried by heating to 130° C. under reduced pressure. This yields a light yellow water-dispersible wax.

The value of n, determined by NMR, is 12.5.

The cloud point of a solution of 5% strength, in a butyldiglycol/water mixture containing 25% by weight of butyldiglycol, is 76° C.

Thioether number: 1.04 meq/g.

EXAMPLE 11

Preparation of a mixture of compounds, of the formula:

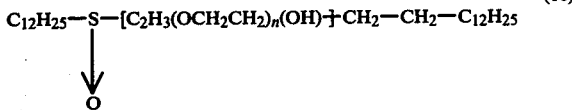

(16)

in which n represents an average statistical value of 12.5.

0.7 ml of hydrogen peroxide of 200 volumes strength is added, at 30° C., to 12 g of the mixture of compounds prepared in accordance with Example 10(b), dissolved in 20 ml of methanol. The temperature is kept between 30° and 45° C. for 2 hours and the mixture is then left at ambient temperature for 48 hours. The methanol is distilled under reduced pressure. The product thus obtained is in the form of a yellow-coloured water-dispersible paste.

The cloud point of a solution of 5% strength, in a butyldiglycol/water mixture containing 25% by weight of butyldiglycol, is 71° C.

EXAMPLE 12

Preparation of a mixture of compounds, of the formula:

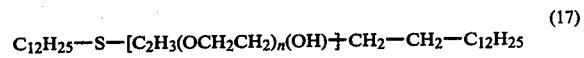

(17)

in which n denotes an average statistical value of 26.

0.5 ml of a solution of sodium methylate in methanol, containing 6 meq/g, is added to 44 g of the crude mixture of compounds obtained in accordance with Example 10(b) and in the molten state. The methanol is distilled under reduced pressure, the mixture is then heated to 160° C. under a nitrogen atmosphere and 30 g of ethylene oxide are added. The crude product thus obtained is dissolved in its own weight of n-butan-1-ol and washed twice with 150 ml of boiling water. After removing the solvents by heating at 130° C. under reduced pressure, a wax is obtained which dissolves in water to give a slight turbidity.

The value of n, determined by NMR, is 26.

The cloud point of a solution of 5% strength by weight, in a butyldiglycol/water mixture containing 25% by weight of butyldiglycol, is 85° C.

Thioether number: 0.63 meq/g.

EXAMPLE 13

Preparation of a mixture of compounds, of the formula:

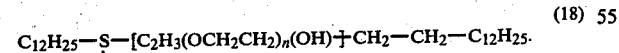

(18)

in which n denotes an average statistical value of 26.

0.7 ml of hydrogen peroxide of 200 volumes strength is added, at 25° C., to 20 g of the mixture of compounds obtained in accordance with Example 12, dissolved in 30 ml of methanol. The mixture is left at ambient temperature for 24 hours and then heated at 50° C. for 2 hours. The methanol is then distilled under reduced pressure.

The product thus obtained is a yellow watersoluble paste.

The cloud point of a solution of 5% strength, in a butyldiglycol/water mixture containing 25% by weight of butyldiglycol, is 80° C.

APPLICATION EXAMPLES

EXAMPLE A1

Moisturising composition for dry skin 4.8 g of the compounds obtained in accordance with Example 2 and 3.2 g of cholesterol are carefully mixed at 90° C. 20 g of a 2% strength aqueous solution of sodium pyrrolidonecarboxylate are then added.

The mixture is brought gradually back to ambient temperature and 172 g of a 2% strength aqueous solution of sodium pyrrolidonecarboxylate are added.

After dispersing the mixture for 1 hour with the aid of an ultra-disperser, small spheres with an average size of less than one micron are obtained.

This composition is used in the treatment of dry skin.

EXAMPLE A2

Fluid body emulsion 10 g of the product obtained in accordance with Example 5 are solubilised in 40 g of liquid petrolatum. 50 g of water are then introduced at 80° C., whilst stirring vigorously. The mixture is left to cool, whilst stirring.

A fine water-in-oil emulsion is thus obtained, which is very pleasant to apply, like a beauty milk.

EXAMPLE A3

| Body milk | |
|---|---|
| Mixture of compounds according to Example 8 | 10 g |
| Liquid petrolatum | 40 g |
| Perfume | 0.2 g |
| Preservative | 0.1 g |
| Distilled water q.s.p. (amount sufficient for) | 100 g |

The compounds of Example 8 are dissolved in the liquid petrolatum at 85° C. The water, also at 85° C., is slowly added to the solution, whilst stirring vigorously. The mixture is left to cool to ambient temperature, whilst stirring.

This yields an oil-in-water emulsion in the form of a fairly fluid white milk which is easy to spread.

EXAMPLE A4

| Face milk | |
|---|---|
| Mixture of compounds of Example 8 | 3.3 g |
| Mixture of compounds of Example 9 | 6.6 g |
| Liquid petrolatum | 40 g |
| Perfume | 0.25 g |
| Preservative | 0.1 g |
| Distilled water q.s.p. | 100 g |

An oil-in-water emulsion is prepared as in Example A3. The resulting emulsion is easy to spread on the skin and imparts a soft feel to the skin.

EXAMPLE A5

| Eye make-up removal lotion. | |
|---|---|
| Mixture of compounds of Example 6 | 4.00 g |
| Hexylene glycol | 1.00 g |

-continued

| Eye make-up removal lotion. | |
| --- | --- |
| Allantoin | 0.05 g |
| Phosphate buffer q.s.p. pH 7.2 | 0.017 g |
| Potassium salt of ethylenediaminetetraacetic acid | |
| Perfume | 0.25 g |
| Preservative | 0.1 g |
| Sterile demineralised water q.s.p. | 100 g |

EXAMPLE A6

| Toilet cream. | |
| --- | --- |
| Mixture of compounds of Example 6 | 4.00 g |
| Cetyl alcohol | 1.2 g |
| Glycerol monostearate | 4.8 g |
| Liquid petrolatum | 30.0 g |
| High molecular weight carboxyvinylic polymer derived from acrylic acid and sold under the trademark "Carbopol 940" | 0.4 g |
| Triethanolamine | 0.4 g |
| Perfume | 0.3 g |
| Preservative | 0.15 g |
| Sterile demineralised water q.s.p. | 100 g |

EXAMPLE A7

| Toning emulsion for the skin. | |
| --- | --- |
| Mixture of compounds according to example 3 | 5.00 g |
| Propylene glycol | 5.20 g |
| Rose water | 30.00 g |
| Preservative | 0.1 g |
| Sterile demineralised water q.s.p. | 100 g |

EXAMPLE A8

| Make-up foundation. | |
| --- | --- |
| Mixture of compounds according to Example 3 | 9.00 g |
| Liquid petrolatum | 10 g |
| Cetyl laurate | 14 g |
| Isopropyl myristate | 4 g |
| Ethylene glycol | 5 g |
| Mixture of aluminium silicate and magnesium silicate, sold under the trademark "Veegum" by Vanderbilt, Connecticut, USA | 1 g |
| Carboxymethylcellulose | 0.5 g |
| Pigments | 3.0 g |
| Perfume | 0.3 g |
| Preservative | 0.2 g |
| Sterile demineralised water q.s.p. | 100 g |

EXAMPLE A9

| After shampoo composition. | |
| --- | --- |
| Mixture of compounds according to Example 8 | 1.00 g |
| Perfume | 0.2 g |
| Preservative | 0.1 g |
| Water q.s.p. | 100 g |

A dispersion is prepared which is applied to wet hair after shampoo.

After drying the hair combs out easily. After setting the hair was found full of life, softer and more glossy. The hold of the set was improved.

We claim:

1. A polyoxyethyleneated non-ionic surfactant compound having the formula $$R-X+C_2H_3(OCH_2CH_2)_n(OH)+CH_2-Y-R'$$

wherein

X represents a sulfur atom or a sulfoxide group,
Y represents methylene,
R and R' each independently represent alkyl having 6 to 20 carbon atoms, or alkenyl having 6 to 20 carbon atoms, the sum of the number of carbon atoms in R and R' being 22 to 30, and
n is a number ranging from 1 to 40.

2. A polyoxyethyleneated non-ionic surfactant compound having the formula $$R-X+C_2H_3(OCH_2CH_2)_n(OH)+CH_2-Y-R'$$

wherein

X represents oxygen,
Y represents a sulfur atom or a sulfoxide group
R and R' each independently represent alkyl having 6 to 20 carbon atoms, or alkenyl having 6 to 20 carbon atoms, the sum of the number of carbon atoms in R and R' being 24 to 32, and
n is a number ranging from 1 to 40.

3. A polyoxyethyleneated non-ionic surfactant compound having the formula $$R-X+C_2H_3(OCH_2CH_2)_n(OH)+CH_2-Y-R'$$

wherein

X represents a sulfur atom or a sulfoxide group,
Y represents a sulfur atom, a sulfoxide group or methylene,
R and R' each independently represent alkyl having 6 to 20 carbon atoms, or alkenyl having 6 to 20 carbon atoms, the sum of the number of carbon atoms in R and R' being 24 to 32 when Y represents a sulfur atom or a sulfoxide group and 22 to 30 when Y represents methylene, and
n is a number ranging from 1 to 40.

4. The polyoxyethyleneated non-ionic surfactant compound of claim 1 wherein R is selected from the group consisting of hexyl, octyl, decyl, dodecyl, tetradecyl, hexadecyl, octadecyl, eicosyl, 2-ethylhexyl, 2-hexyldecyl, 2-octyldodecyl, 1-methylundecyl, 1-methyldodecyl, 1-methyltridecyl, 1-methyltetradecyl, 1-methylpentadecyl, undecenyl and oleyl; and R' is selected from the group consisting of hexyl, octyl, decyl, dodecyl, tetradecyl, hexadecyl, octadecyl and eicosyl.

5. The polyoxyethyleneated non-ionic surfactant compound of claim 2 wherein R is selected from the group consisting of hexyl, octyl, decyl, dodecyl, tetradecyl, hexadecyl, octadecyl, eicosyl, 2-ethylhexyl, 2-hexyldecyl, 2-octyldodecyl, 1-methylundecyl, 1-methyldodecyl, 1-methyltridecyl, 1-methyltetradecyl, 1-methylpentadecyl, undecenyl and oleyl; and R' is selected from the group consisting of hexyl, octyl, decyl, dodecyl, tetradecyl, hexadecyl, octadecyl and eicosyl.

6. The polyoxyethyleneated non-ionic surfactant compound of claim 3 wherein R is selected from the group consisting of hexyl, octyl, decyl, dodecyl, tetradecyl, hexadecyl, octadecyl, eicosyl, 2-ethylhexyl, 2-hexyldecyl, 2-octyldodecyl, 1-methylundecyl, 1-methyldodecyl, 1-methyltridecyl, 1-methyltetradecyl, 1-methylpentadecyl, undecenyl and oleyl; and R' is selected from the group consisting of hexyl, octyl, decyl, dodecyl, tetradecyl, hexadecyl, octadecyl and eicosyl.

* * * * *